United States Patent [19]

Diani et al.

[11] Patent Number: 5,578,599
[45] Date of Patent: Nov. 26, 1996

[54] STIMULATION OF HAIR GROWTH WITH MINOXIDIL AND A 5α-REDUCTASE INHIBITOR

[75] Inventors: Arthur R. Diani, Mattawan; Allen E. Buhl; Heinrich J. Schostarez, both of Portage, all of Mich.

[73] Assignee: The Upjohn Company, Kalamazoo, Mich.

[21] Appl. No.: 376,468

[22] Filed: Jan. 20, 1995

Related U.S. Application Data

[63] Continuation of Ser. No. 9,451, filed as PCT/US91/05170, Jul. 29, 1991, abandoned, which is a continuation of Ser. No. 565,777, Aug. 10, 1990, abandoned.

[51] Int. Cl.$^6$ .......................... A61K 31/505; A61K 31/44
[52] U.S. Cl. ........................................ 514/275; 514/284
[58] Field of Search .................................. 514/284, 275

[56] References Cited

U.S. PATENT DOCUMENTS

| | | | |
|---|---|---|---|
| 4,139,619 | 2/1979 | Chidsey, III | 424/45 |
| 4,596,812 | 6/1986 | Chidsey, III et al. | 514/256 |
| 4,684,635 | 8/1987 | Orentreich et al. | 514/170 |
| 5,026,691 | 6/1991 | Kligman et al. | 514/171 |

FOREIGN PATENT DOCUMENTS

| | | | |
|---|---|---|---|
| 0285382A2 | 10/1988 | European Pat. Off. | A61K 31/58 |
| 3615396A | 11/1987 | Germany | A61K 07/06 |
| 1305017A | 12/1989 | Japan | A61K 07/06 |
| WO87/00427 | 1/1987 | WIPO | A16K 07/06 |

*Primary Examiner*—Marianne M. Cintins
*Assistant Examiner*—M. Moezie
*Attorney, Agent, or Firm*—Donald L. Corneglio

[57] ABSTRACT

An improved method and composition for promoting hair growth in mammals for treating various forms of alopecia or male pattern baldness comprising the concomitant administration of potassium channel openers, such as minoxidil, cromakalim, pinacidil, or a compound selected frown the classes of s-triazine, thiane-1-oxide, benzopyran and pyridinopyran compounds; and a 5α-reductase inhibitors, 17β-(N-tert-butylcarbamoyl)-4-aza-5-α-androst-1-en-3-one. The method comprises administering an effective amount of the potassium channel opener and administering an effective amount of the 17β-(N-tert-butylcarbamoyl)-4-aza-5-α-androst-1-en-3-one whereby the promotion of hair growth is increase over the sole administration of the potassium channel opener.

4 Claims, No Drawings

STIMULATION OF HAIR GROWTH WITH MINOXIDIL AND A 5α-REDUCTASE INHIBITOR

CROSS-REFERENCE TO RELATED APPLICATIONS

This application is a continuation of U.S. Ser. No. 08/009,451, filed 27 Jan. 1993, abandoned; which was a continuation of International Patent Application No. PCT/US91/05170, filed 29 Jul. 1991; which was a continuation of U.S. Ser. No. 07/565,777, filed 10 Aug. 1990, abandoned.

BACKGROUND OF THE INVENTION

The present invention relates to improved methods and compositions for promoting hair growth by the concomitant administration of a potassium channel opener such as minoxidil, cromakalim, pinacidil, or a compound selected from the classes of potassium channel openers such as s-triazine derivatives, benzopyran derivatives, pyridinopyran derivatives and thiane-1-oxide compounds; and a 5α-reductase inhibitors, 17β-(N-tert-butylcarbamoyl)-4-aza-5-α-androst-1-en-3-one.

Since the discovery that minoxidil could promote hair growth and was useful in the treatment of androgenetic alopecia commonly known as "male pattern baldness" (U.S. Pat. Nos. 4,596,812; 4,139,619), alopecia areata, and balding in females, effort has been directed toward attempts to improve upon the sole use of a topical minoxidil composition by incorporating other active ingredients, for example the combinations of minoxidil/hydrocortisone and minoxidil/retinoids (DE 3827467-A).

Another approach has been to attempt to identify and quantify the biological mechanisms responsible for the initiating and controlling hair growth at the follicullar level and intervening with therapeutic agents which stimulate hair growth. It is well known in the art that the onset of puberty results in changes in endocrine levels which result in, among other changes, the stimulation of facial hair growth (males), axillary hair growth (males and females), and pubic hair growth (males and females). One class of compounds implicated in these effects are the androgens.

Androgens appear to play a major role in the development and progression of androgenetic alopecia (male pattern baldness). Rittmaster, R. S., *Clin. Dermatol.*, 6, 122 (1988). This was demonstrated in humans, in that prepubertally castrated men do not develop male pattern baldness. Hamilton, J. B., *Am. J. Anat.*, 71, 451 (1942). In the skin, and presumably in the follicle, the effector androgen is dihyrdotestosterone (DHT), the product of the enzymatic conversion of testosterone to DHT by the enzyme 5α-reductase. Ebling, F. J. *Clin. Endocrinol. Metab.*, 15, 319 (1986); Price, V. H. *Arch. Dermatol.*, 111, 1496 (1975). Additional evidence for DHT's role stems from reports that men with male pattern baldness have elevated 5α-reductase levels in the hair follicles and skin of the frontal scalp and that men with a 5α-reductase deficiency do not develop male pattern baldness. Bingham, K. D., Shaw, D. A., *J. Endocrinol.*, 57, 111 (1973); Schweikert, H. U., Wilson, J. D., *J. Clin. Endocrinol. Metab.*, 385, 811 (1974). Antiandrogen therapy offers a potential intervention to the treatment of male pattern baldness in men, and in women where it has been suggested that elevated androgen levels are responsible for the appearance of male pattern baldness. Rittmaster, R. S., Lofiaux, D. L., *Ann. Intern. Med.*, 106, 95 (1987). This class of compounds, the antiandrogens, have been subdivided into two major catagories, the androgen receptor blockers and the 5α-reductase inhibitors. Androgen receptor blockers interfere with the binding of androgens, testosterone and dihydrotestosterone (DHT), to their receptors, while 5α-reductase inhibitors prevent the conversion of testosterone into DHT. The clinical use of androgen blockers, such as cyproterone acetate, in men is complicated with systemic effects on normal sexual function. This is not the case in women, where these agents are utilized. Burke, B. M., Cunliff, W. J., *Br. J. Dermatol.*, 112, 124 (1985); Dawber, R. P. R., Sonnex, T., Ralfs, I., *Br. J. Dermatol., Suppl.* 107, 20 (1982). The other class of antiandrogens are the 5α-reductase inhibitors. These compounds block action of 5α-reductase and thus reduce the level of DHT in the peripheral tissue. Rittmaster, R. S, Stoner, E., Thompson, D. L., Nance, D., Lasseter, K. C., *J. Androl.*, 10, 259 (1989). Brooks, J. R., Berman, C., Primka, R. L., Reynolds, G. F., Rasmusson, G. H., *Steroids*, 47, 1 (1986). Rittmaster, R. S., Uno, H., Povar, M. L., *J. Clin. Endocrinol. Metab.*, 65, 188 (1987) have shown that topical treatment of periadolescent stumptail macaque moneys with the 5α-reductase inhibitor 4-MA prevented the progression of baldness normally observed in this species. Similar studies in humans have not been reported.

The coupling of hair growth stimulation with potassium channel activation has been inferred from literature reports of several vasodilators, minoxidil (through its metabolite minoxidil sulfate), pinacidil, and diazoxide, which cause varying degrees of hypertrichosis upon oral administration. Zins, G. R., *Clin. Dermatol.*, 6, 132 (1988); Goldberg, M. R., *J. Cardiovasc. Pharmacol.*, 12(Suppl. 2), S41 (1988); Okun, R., Russell, R. P., Wilkson, W. R., *Arch Inter. Meal.*, 112, 886 (1963). It is also known in the an that topical minoxidil is an effective treatment for andogentic alopecia. The mechanism by which these compounds, minoxidil (through its metabolite minoxidil sulfate), pinacidil, and diazoxide, dilate vascular smooth muscle has been reported to be via the opening (activation) of potassium channels. Robertson, D. W., Steinberg, M. I., *J. Med. Chem.*, 33, 1529 (1990). Thus potassium channel openers are useful in the treatment of androgenetic alopecia.

The surprising and unexpected result, and the subject of this invention, is the synergistic effect observed when both 17β-(N-tert-butylcarbamoyl)-4-aza-5-α-androst-1-en-3-one and minoxidil, a potassium channel opener, are utilized to stimulate or promote hair growth in a statistically significant fashion when compared to each drug alone.

INFORMATION DISCLOSURE STATEMENT

Topical minoxidil has been shown to be an effective treatment for male pattern baldness as described in U.S. Pat. Nos. 4,596,812 and 4,139,619. The utilization of 17β-(N-tert-butylcarbamoyl)-4-aza-5-α-androst-1-en-3-one for the treatment of androgenetic alopecia has been disclosed in European Patent Application 285 382 A2. The use of combinations of androgen receptor blocking agent (antiandrogen) and 5α-reductase inhibitors (not 17β-(N-tert-butylcarbamoyl)-4-aza-5-α-androst-1-en-3-one) has been disclosed in U.S. Pat. No. 4,684,635. The combination of minoxidil and an androgen receptor blocking agent for the treatment of male pattern baldness has also been disclosed in Patent Applications DE 3615-396-A and WO 8700-427-A. The combination of minoxidil and a 5α-reductase inhibitor for the treatment of male pattern baldness has also been disclosed in Japanese Patent Application JA 1305-017-A.

SUMMARY OF THE INVENTION

In one aspect, the subject invention is directed toward an improved method for promoting hair growth in mammals comprising the administration of a potassium channel opener in an effective amount and the administration of 17β-(N-tert-butylcarbamoyl)-4-aza-5-α-androst-1-en-3-one in an effective amount whereby hair growth is increased over the sole administration of the potassium channel opener. The routes of administration for either component can be by any of various means, preferably orally, topically or any combination of the two. More preferably and conveniently, the two components are applied together topically.

The potassium channel opener can be administered topically in an amount of from about 0.01 to about 20 percent by weight, or orally in an amount of from about 0.001 m about 50 mg/kg body weight. The 17β-(N-tert-butylcarbamoyl)-4-aza-5-α-androst-1-en-3-one can be administered topically in an amount of from about 0.01 to about 10 percent by weight of composition or administered orally in an amount of from about 0.001 to about 10 mg/kg body weight. The potassium channel opener and/or 17β-(N-tert-butylcarbamoyl)-4-aza-5-α-androst-1-en-3-one is generally administered in a pharmaceutical carder adapted for oral administration or in a pharmaceutical acceptable carder adapted for topical application.

Preferably, the potassium channel opener and 17β-(N-tert-butylcarbamoyl)-4-aza-5-α-androst-1-en-3-one are combined into a pharmaceutical carrier adapted for topical application. The potassium channel opener can be routinely applied to an area of treatment concomitant with the administration of 17β-(N-tert-butylcarbamoyl)-4-aza-5-α-androst-1-en-3-one.

The potassium channel opener is minoxidil, cromakalim, pinacidil, or a compound selected from the chemical classes of s-triazines, thiane-1-oxides, benzopyrans, pyridinopyrans and derivatives thereof or a pharmaceutically acceptable salt thereof.

In another aspect, the subject invention is directed toward a pharmaceutical composition comprising an effective amount of a potassium channel opener, an effective amount of 17β-(N-tert-butylcarbamoyl)-4-aza-5-α-androst-1-en-3-one and a pharmaceutical carder adapted for topical application. The pharmaceutical carrier can be petrolatum, lanolin, propylene glycol, N-methyl-2-pyrrolidinone, polyethylene glycol, oleyl alcohol, ethyl alcohol or mixtures thereof.

DETAILED DESCRIPTION OF THE INVENTION

The present invention relates to a method for promoting hair growth which means to increase normal hair growth or restore hair growth in mammals, including humans, suffering from hair growth disorders such as alopecia or male pattern baldness. The promotion or restoration of hair growth has been discovered to be significantly enhanced by the concomitant administration of a potassium channel openers (activators); and a 5α-reductase inhibitor, 17β-(N-tert-butylcarbamoyl)-4-aza-5-α- androst-1-en-3-one.

Typical examples of "potassium channel openers" or "potassium channel opener vasodilators" as contemplated by the subject invention arc minoxidil, cromakalim, pinacidil, and those compounds selected from the chemical classes of s-triazines, benzopyran, pyridinopyran and thiane-1-oxides their derivatives and pharmaceutically acceptable salts.

Minoxidil is chemically, 6-amino-1,2-dihydro-hydroxy-2-imino-4-piperidinopyrimidine and analogs thereof. The preparation or these compounds arc described in U.S. Pat. Nos. 3,382,247, 3,451,451 and 3,644,354 and J. M. McCall, et al., *J. Org. Chem.*, 40, 3304 (1975). Related compounds are sulfoxypyrimidinium, -pyridinium, and -triazinium which are described in U.S. Pat. No. 4,287,338 herein incorporated by reference. Hereinafter, the term "minoxidil" means any of the various forms of 6-amino-1,2-dihydro-hydroxy-2-imino-4-pipefidinopyrimidine, derivatives and analogs thereof. Minoxidil is distributed by The Upjohn Company, Kalamazoo, Mich.

Cromakalim is chemically, (3S-trans) 3,4-dihydro-3-hydroxy-2,2-dimethyl-4-(2-oxo-1-pyrrolidinyl)-2H-1-benxopyran -6-carbonitrile a molecular wight of 285.33 g. and a melting point of 224.5°–225.5° C. Cromakalim is distributed by SmithKline Consumer Products, Philadelphia, Penna.

Pinacidil is chemically, N-cyano-N'-4-pyridinyl-N"-(1,2, 2-trimethylpropyl)-guanidine monohydrate, a molecular weight of 263.34 g. and a melting point of 110°–116° C. The preparation of pinacidil is described in U.S. Pat. No. 4,057, 535 and German Patent 2,557,438 and is distributed by Eli Lilly and Company, Indianapolis, Ind.

s-Triazine compounds or 2,5-diamino-4-substituted-s-triazine-1-oxides are described in U.S. Pat. No. 3,270,014 assigned to The Upjohn Company, Kalamazoo, Mich. Specific examples of these compounds include: N4-hexyl-2,4, 6-triamino-1,3,5-triazine-1-oxide; N4-butyl-2,4,6-triamino-1,3,5-triazine-1-oxide; N4-pentyl-2,4,6-triamino-1,3,5-triazine-1-oxide; 4-(N,N-dipropyl)-2,6-diamino-1,3,5-triazine-1-oxide; 4-(N,N-dibutyl)-2,5-diamino-1,3,5-triazine-1-oxide; 4-(1-pyrollidinyl)-2,6-diamino-1,3,5-triazine-1-oxide; 4-(N,N-di(2-methyl-2-propenyl)amino)-2, 6-diamino-1,3,5-triazine-1-oxide; 4-(N,N-(diallylamino)-2, 6-diamino-1,3,5-triazine-1-oxide; 4-(N,N-dimethylamino)-2,6-diamino-1,3,5-triazine-1-oxide; 4-(1-piperdinyl)-2,6-diamino-1,3,5-triazine-1-oxide; N4-propyl-2,4,6-triamino-1,3,5-triazine-1-oxide; N4-ethyl-2,4,6-triamino-1,3,5-triazine-1-oxide; N4-(1,1,4,4-tetramethylbutyl)-2,4,6-triamino-1,3,5-triazine-1-oxide; and N4-heptyl-2,4,6-triamino-1,3,5-triazine-1-oxide.

Thiane-1-oxide compounds are described in U.S. Pat. No. 4,568,682 assigned to Rhone-Poulenc Sante, Courbevoie, France. An example of such a compound contemplated by the subject invention is N-methyl-2-(pyridin-3-yl)tetrahydrothiopyran-2-carbothioamide-1-oxide.

Other potassium channel openers include pyranopyridine derivatives described in patent applications GB 2 204 868 A and benzopyran derivatives described in patent applications GB 2 204 868 A, EP 314 446 A2, EP 339 562 A, EP 340 718 A, EP 337 179, AU A 18556/88, JA 1294 677 A, EP 359 537 A, and U.S. Pat. No. 4,900,752.

Pharmaceutically acceptable salts of the potassium channel openers are for example acid addition salts which may be chosen from the following: acetate, adipate, alginate, aspartate, benzoate, benzenesulfonate, bisulfitte, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate.

Pharmaceutically acceptable cationic addition salts of the potassium channel openers include: pharmacologically acceptable metal cations, ammonium, amine cations, or quaternary ammonium cations. Especially preferred metal cations are those derived from the alkali metals, e.g., lithium, sodium, and potassium, and from the alkaline earth metals, magnesium and calcium, although cationic forms of other metals, e.g., aluminum, zinc, and iron are also within the scope of this invention. Pharmacologically acceptable amine cations are those derived from primary, secondary, and tertiary amines.

The second essential, active ingredient of the subject invention is the compound 17β-(N-tert-butylcarbamoyl)-4-aza-5-α-androst-1-en-3-one, (hereinafter referred to as "TBCAA") which has a molecular weight of 372.56. This compound is a 5α-reductase inhibitor and is described in European Patent Application 88302807.8, Publication No. 0285382, published 5 Oct. 1988, assigned to Merck & Co., Inc., Rahway, N.J. This publication discloses various analogs of TBCAA all of which are disclosed to be active as testosterone 5α-reductase inhibitors and thus are useful for the treatment of androgenic alopecia, including male pattern alopecia. The preferred administration of TBCAA is topical. TBCAA can be administered by any of various routes as well as can be the potassium channel opener.

Administration routes for the two components of the subject invention can be topically, orally, parenterally or rectally. Typically, TBCAA is administered either topically with the potassium channel opener or orally while the potassium channel opener is applied topically. Preferably and most conveniently, the administration route would be to compound TBCAA with a potassium channel opener in a pharmaceutical, topical vehicle.

Typically, the potassium channel opener and optionally the 17β-(N-tert-butylcarbamoyl)-4-aza-5-α-androst-1-en-3-one compound are applied to the skin region where hair growth is desired with a pharmaceutical carrier. More preferably, the pharmaceutical carrier is adopted for topical application such as those pharmaceutical forms which can be applied externally by direct contact with the surface to be treated.

Conventional pharmaceutical forms for this purpose include ointments, waxes, gels, lotions, pastes, jellies, sprays, aerosols, and the like in aqueous or nonaqueous formulations. The term "ointment" embraces formulations (including creams) having oleaginous, absorption, water-soluble and emulsion-type bases, e.g., petrolatum, lanolin, polyethylene glycols, N-methyl-2-pyrrolidinone, oleyl alcohol as well as mixtures of these.

Preparation of minoxidil topical compositions are disclosed in U.S. Pat. Nos. 4,139,619 and 4,596,812, both herein incorporated by reference, as examples of how to prepare topical compositions for any of the potassium channel openers and/or the 17β-(N-tert-butylcarbamoyl)-4-aza-5-α-androst-1-en-3-one Additionally, the potassium channel openers and/or the 17β-(N-tert-butylcarbamoyl)-4-aza-5-α-androst-1-en-3-one compound can be admixed with other compounds for the treatment of hair growth. Such compounds which can be included in the overall composition or treatment are various combinations of the potassium channel openers, vasoconstrictors such as betamethasone dipropionate, corticosteroids such as hydrocortisone, scopolamine, and antiandrogens such as cyoctol, and cyproterone acetate.

Typically, a potassium channel opener is used in an effective amount that is all amount sufficient to promote hair growth or treat hair growth disorders such that hair growth is increased or produced. The potassium channel opener is added in an amount of from about 0.001 to about 10, preferably, 0.01 to about 5 percent by weight of the composition.

The 17β-(N-tert-butylcarbamoyl)-4-aza-5-α-androst-1-en-3-one compound is used in an effective amount, that is, an amount sufficient to promote hair growth or treat hair growth disorders such that hair growth is increased or produced over that which would be increased or produced by the administration of a potassium channel opener alone. The testosterone 5α-reductase inhibitor, TBCAA, is added in an amount of from about 0.0001 to about 10, preferably, 0.001 to about 5 percent by weight of the composition.

In a topical application, the compound or formulated composition can be applied to the area to be treated, in mammals such as the scalp in humans, by spraying, dabbing or swabbing. Other less specific methods can be employed provided the active ingredient(s) are delivered to the region of a hair follicle. Preferably, the compound or formulated composition is periodically applied to the treatment area on a routine basis prior to, during and subsequent to hair growth. Generally, the routine treatment would be to apply the compound or formulated composition at least daily, preferably twice daily although more frequent applications can be used. The percentage by weight of the active ingredients, potassium channel opener and 17β-(N-tert-butylcarbamoyl)-4-aza-5-α-androst-1-en-3-one compound herein utilized ranges from an effective amount which is an amount sufficient to increase normal hair growth or treat various forms of alopecia whereby the hair growth is significantly more than if either of the compounds were solely administered. In topical preparations the pharmaceutical carder for topical applications constitutes a major amount of the preparation. Typically, the active ingredient is in a range of from about 0.01 to about 10 percent total weight of the topical composition, preferably 0.1 to 5 percent total weight.

Experimentation

The following protocol was utilized with the stumptail macaque monkey to demonstrate the synergistic affect of minoxidil and 17β-(N-tert-butylcarbamoyl)-4-aza-5-α-androst-1-en-3-one "CTBCAA") for promoting hair growth.

Twenty-one male stumptail macaque (*Macaca specoisa*) monkeys were assigned to vehicle control and drug treated groups on the basis of baseline hair weight data. This assignment procedure was necessary to insure that the average baseline hair growth for each control and experimental group was comparable. The control and drug treatment groups were as follows:

1. Topical 50:30:20 vehicle (N-6)
2. Oral TBCAA and topical 50:30:20 vehicle (N=5)
3. Oral TBCAA and topical 100mM minoxidil (N=5)
4. Topical 100mM minoxidil (N=5).

The vehicle consisted of 50% propylene glycol, 30% ethanol, and 20% water. The 100 mM concentration of topical minoxidil was formulated in this vehicle. TBCAA was prepared as an oral dose of 0.5 mg per monkey (interanimal weight range of 9.5–15.5 kg). Immediately prior to the dosing phase of the study, hair was removed from a 1 inch square area (identified by four tattoos) in the center of the balding scalp. This hair collection was the baseline hair growth determination prior to the beginning of treatment. Approximately 250μL of vehicle or 100 mM minoxidil (prepared in vehicle) were topically administered to the tattooed area of the scalp. For the groups which received combined topical and oral dosing, 0.5 mg/monkey TBCAA was ingested by the monkeys at the same time as the topical dose was administered. The monkeys were dosed once per day, seven days per week for twenty weeks.

At four week intervals throughout the dosing phase of the study, each monkey was shaved and the hair was collected and weighed. The body weight data (at baseline and during assay) were analyzed by the nonparametric Wilcoxon rank-sum test. Differences were significant at p<0.05. The hair weight data (mean±SEM) at each 4 week collection for vehicle and treatment groups were expressed as the change from baseline. Statistical analysis (ANOVA) was performed on the ranks of the data to show overall differences among groups at each 4 week collection with p<0.10 marginally significant, p<0.05 significant, and p<0.01 highly significant.

Results

The data reported in Tables I and II were obtained after 12 weeks of dosing, Tables III and IV after 16 weeks of dosing and in Tables V and VI after 20 weeks of dosing. They show that the combination of TBCAA and minoxidil is statistically superior in promoting hair growth, in this model, than the constituent agents alone.

After twelve weeks:

TABLE I

| Group | Hair Growth (mg)[1] | p vs Vehicle |
| --- | --- | --- |
| TBCAA | +1.4 ± 2.5 | 0.44 |
| MINOXIDIL | +2.6 ± 1.0 | 0.20 |
| MINOXIDIL + TBCAA | +7.6 ± 1.6 | 0.002 |
| Vehicle | −0.3 ± 1.0 | — |

TABLE II

| Group | Hair Growth (mg)[1] | p vs TBCAA/Minoxidil |
| --- | --- | --- |
| TBCAA | +1.4 ± 2.5 | 0.02 |
| MINOXIDIL | +2.6 ± 1.0 | 0.05 |
| MINOXIDIL + TBCAA | +7.6 ± 1.6 | — |
| Vehicle | −0.3 ± 1.0 | 0.002 |

[1]Cumulative change in hair weight from baseline.

After sixteen weeks:

TABLE III

| Group | Hair Growth (mg)[1] | p vs Vehicle |
| --- | --- | --- |
| TBCAA | +2.7 ± 2.3 | 0.09 |
| MINOXIDIL | +3.1 ± 1.0 | 0.06 |
| MINOXIDIL + TBCAA | +10.9 ± 1.6 | 0.001 |
| Vehicle | −1.0 ± 1.0 | — |

TABLE IV

| Group | Hair Growth (mg)[1] | p vs TBCAA/Minoxidil |
| --- | --- | --- |
| TBCAA | +2.7 ± 2.3 | 0.002 |
| MINOXIDIL | +3.1 ± 1.0 | 0.002 |
| MINOXIDIL + TBCAA | +10.9 ± 1.6 | — |
| Vehicle | −1.0 ± 1.0 | 0.001 |

[1]Cumulative change in hair weight from baseline.

After twenty weeks:

TABLE V

| Group | Hair Growth (mg)[1] | p vs Vehicle |
| --- | --- | --- |
| TBCAA | +2.2 ± 3.6 | 0.17 |
| MINOXIDIL | +4.4 ± 1.0 | 0.03 |
| MINOXIDIL + TBCAA | +13.5 ± 1.8 | 0.006 |
| Vehicle | −1.3 ± 1.5 | — |

TABLE VI

| Group | Hair Growth (mg)[1] | p vs TBCAA/Minoxidil |
| --- | --- | --- |
| TBCAA | +2.2 ± 3.6 | 0.009 |
| MINOXIDIL | +4.4 ± 1.0 | 0.009 |
| MINOXIDIL + TBCAA | +13.5 ± 1.8 | — |
| Vehicle | −1.3 ± 1.5 | 0.006 |

[1]Cumulative change in hair weight from baseline.

The above data shows a statistically significant increase in the promotion of hair growth which is unexpected despite the know propensity of the potassium channel opener (minoxidil) and the testosterone 5α-reductase inhibitor (TBCAA) to individually affect hair growth. The combination of the two active ingredients therefore represents a significant advancement in the art of promoting, maintaining, or restoring hair growth in mammals.

What is claimed:

1. A method for increasing or restoring hair growth over the sole administration of a topical minoxidil treatment comprising the concomitant administration of:

a topical preparation of minoxidil in an amount sufficient to promote hair growth, applied to an area of skin where hair growth is to be increased or restored; and an oral administration of 17β-(N-tert-butylcarbamoyl)-4-aza-5-α-androst-1-en-3-one in an amount from about 0.05 to about 0.03 mg/Kg to promote hair growth such that hair growth is increased over the administration of minoxidil alone.

2. The method of claim 1 wherein said amount of minoxidil is from about 0.001 to about 10 percent in a topical preparation.

3. The method of claim 2 wherein said amount of minoxidil is from about 0.01 to about 5 percent in a topical preparation.

4. The method of claim 1 wherein said 17β-(N-tert-butylcarbamoyl)-4-aza-5-α-androst-1-en-3-one is in an amount of about 0.5 mg per about 9.5 to about 15.5 kg.

* * * * *